United States Patent [19]

Yang

[11] Patent Number: 5,686,587
[45] Date of Patent: Nov. 11, 1997

[54] INTERMEDIATE FOR AZITHROMYCIN

[75] Inventor: Bingwei V. Yang, Waterford, Conn.

[73] Assignee: Pfizer Inc., New York, N.Y.

[21] Appl. No.: 537,741

[22] PCT Filed: Mar. 14, 1994

[86] PCT No.: PCT/US94/02547

§ 371 Date: Nov. 13, 1995

§ 102(e) Date: Nov. 13, 1995

[87] PCT Pub. No.: WO94/26758

PCT Pub. Date: Nov. 24, 1994

Related U.S. Application Data

[63] Continuation of Ser. No. 64,610, May 19, 1993, abandoned.

[51] Int. Cl.$^6$ .............................. C07H 17/08; C08B 01/00
[52] U.S. Cl. .......................... 536/7.1; 514/29; 536/18.5; 536/125
[58] Field of Search .......................... 536/7.2, 17.2, 536/17.3, 17.4, 17.9, 18.5, 7.1, 125; 514/29

[56] References Cited

U.S. PATENT DOCUMENTS

| | | | |
|---|---|---|---|
| 4,328,334 | 5/1982 | Kobrehel et al. | 536/7.4 |
| 4,382,085 | 5/1983 | Sciavolino | 424/180 |
| 4,464,527 | 8/1984 | Bright | 536/7.4 |
| 4,474,768 | 10/1984 | Bright | 424/180 |
| 4,512,982 | 4/1985 | Hauske et al. | 514/29 |
| 4,517,359 | 5/1985 | Kobrehel et al. | 536/7.4 |
| 4,518,590 | 5/1985 | Hauske et al. | 514/7.4 |
| 4,526,889 | 7/1985 | Bright | 514/29 |
| 5,189,159 | 2/1993 | Wilkening | 540/456 |
| 5,202,434 | 4/1993 | Wilkening | 540/454 |

FOREIGN PATENT DOCUMENTS

| | | |
|---|---|---|
| 137132 | 4/1985 | European Pat. Off. . |
| 503932 | 9/1992 | European Pat. Off. . |
| 503949 | 9/1992 | European Pat. Off. . |
| 0508795 | 10/1992 | European Pat. Off. . |
| 508699 | 10/1992 | European Pat. Off. . |
| 508725 | 10/1992 | European Pat. Off. . |
| 508726 | 10/1992 | European Pat. Off. . |

OTHER PUBLICATIONS

Bright et al., J. Antibiotics, vol. XLI, No. 8, 1029–1047 (1988).

Gasc et al., J. Antibiotics, vol. 44, No. 3, No. 313–330 (1991).

Egan et al., J. Org. Chem., vol. 39, No. 17, 2492–2494 (1974).

Djokic et al., J. Chem. Soc. Perkin Trans. I, (1986), 1881–1890.

Jones, J. Org. Chem., vol. 57, 4361–4367 (1992).

*Primary Examiner*—John Kight
*Assistant Examiner*—Howard C. Lee
*Attorney, Agent, or Firm*—Peter C. Richardson; Gregg C. Benson; James T. Jones

[57] ABSTRACT

A compound having formula (III). Also, a process of making azithromycin comprising reducing the compound of formula (III) and N-methylating the reduced product.

11 Claims, No Drawings

INTERMEDIATE FOR AZITHROMYCIN

This is a §371 national stage application of PCT/US94/02547 filed internationally on Mar. 14, 1994, which is a continuation of U.S. application Ser. No. 08/064,610, filed May 19, 1993, now abandoned.

FIELD OF THE INVENTION

This invention relates to antibiotics, and particularly relates (1) to an intermediate per se, useful for making the known antibiotic azithromycin, (2) to a process for making azithromycin with the intermediate, and (3) to processes for making the intermediate.

BACKGROUND OF THE INVENTION

Erythromycin is an antibiotic formed during the culturing of a strain of *Streptomyces erythreus* in a suitable medium as taught in U.S. Pat. No. 2,653,899. Erythromycin, which is produced in two forms, A and B, is represented by the following structure (I):

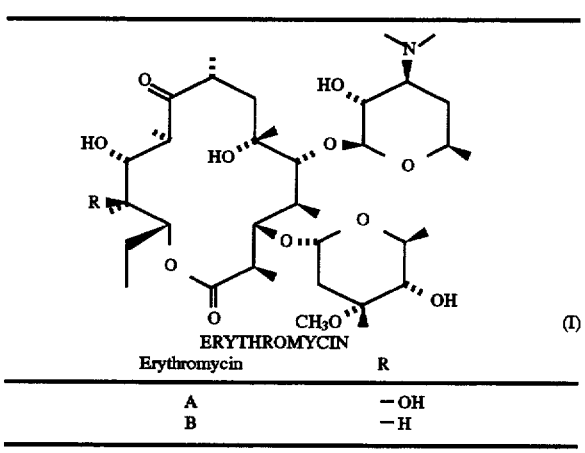

| Erythromycin | R |
|---|---|
| A | —OH |
| B | —H |

The structure reveals that the antibiotic is comprised of three main portions: a sugar fragment known as cladinose, a second sugar moiety containing a basic amino substituent known as desosamine and a fourteen membered lactone ring referred to as erythronolide A or B or as the macrolide ring.

Azithromycin is the U.S.A.N. (generic name) for 9a-aza-9a-methyl-9-deoxo-9a-homoerythromycin A, a broad spectrum antibacterial compound derived from erythromycin A. Azithromycin was independently discovered by Bright, U.S. Pat. No. 4,474,768 and Kobrehel et al., U.S. Pat. No. 4,517,359, and was named N-methyl-11-aza-10-deoxo-10-dihydro-erythromycin A in these patents. It has the following structure (II) wherein the numbering system conventionally employed is shown:

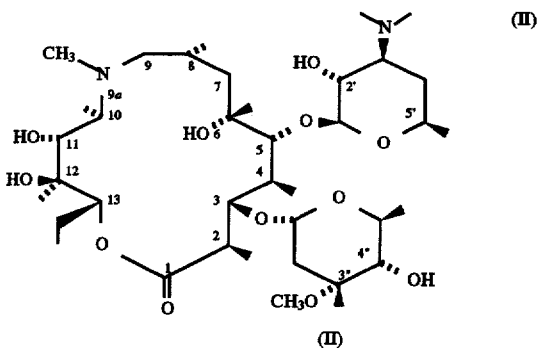

The above patents also disclose that (II) and certain derivatives thereof possess antibacterial properties.

In particular, the procedure for making azithromycin from erythromycin A involves relatively strong reaction conditions as described, for example, in Djokic et al., *J. Chem. Soc. Perkin Trans. I*, 1881, (1986), wherein the preparation of 10-dihydro-10-deoxo-11-azaerythromycin A from an imino ether precursor was effected by catalytic hydrogenation in acetic acid under 70 atm of $H_2$.

SUMMARY OF THE INVENTION

In a first aspect, this invention provides a compound having formula III

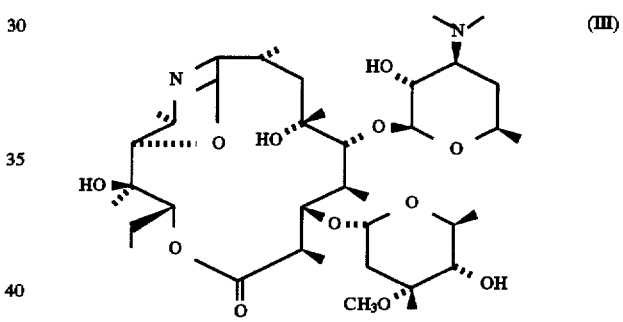

Compound III, 9-deoxo-11-deoxy-9,11-epoxy-9,9a-didehydro-9a-aza-9a-homoerythromycin A, herein also referred to as a 9,11-imino ether, has utility as an intermediate for making azithromycin, and can be reduced to a direct precursor of azithromycin having formula IV, shown below. The precursor of Formula IV need only be N-methylated (position 9a) to produce azithromycin. Accordingly, in a further aspect, this invention provides a process of making azithromycin, comprising reducing the (9,11-imino ether) compound of formula III to 9a-aza-9-deoxo-9a-homoerythromycin A, a compound having formula IV

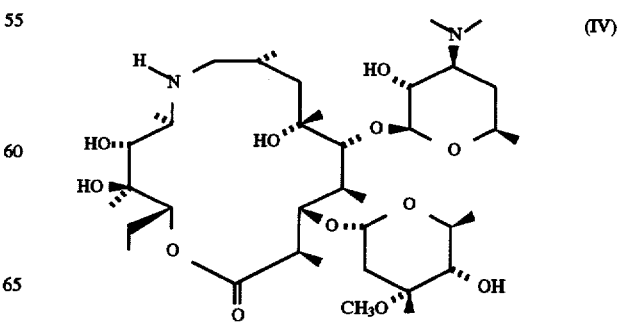

and thereafter N-methylating the said compound of formula IV.

In a further aspect, this invention provides a process of making an intermediate of formula III, comprising isomerizing a compound of formula V, 9-deoxo-6-deoxy-6,9-epoxy-9,9a-didehydro-9a-aza-homoerythromycin A:

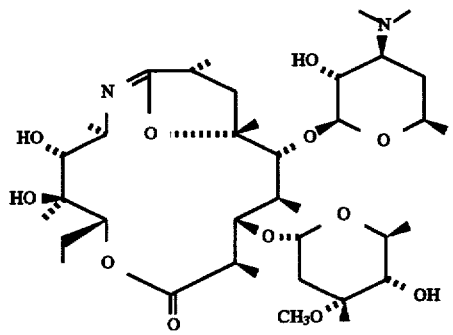

(V)

in a suitable solvent.

In still a further aspect, this invention provides an additional process of making an intermediate of formula III, comprising treating a compound of formula VI

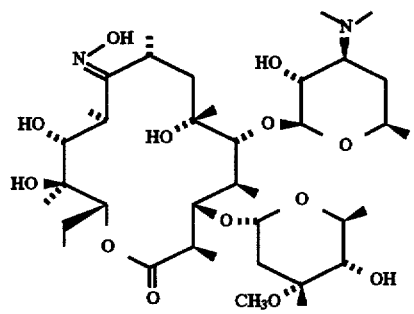

(VI)

with tosyl chloride and pyridine in diethyl ether at a temperature of less than about 10° C. for a time between about 0.5 and about 50 hours.

DETAILED DESCRIPTION

A general reaction scheme for (1) making the intermediate 9,11-imino ether and (2) using the intermediate 9,11-imino ether to make azithromycin is shown in Scheme 1:

Scheme I

STEP A

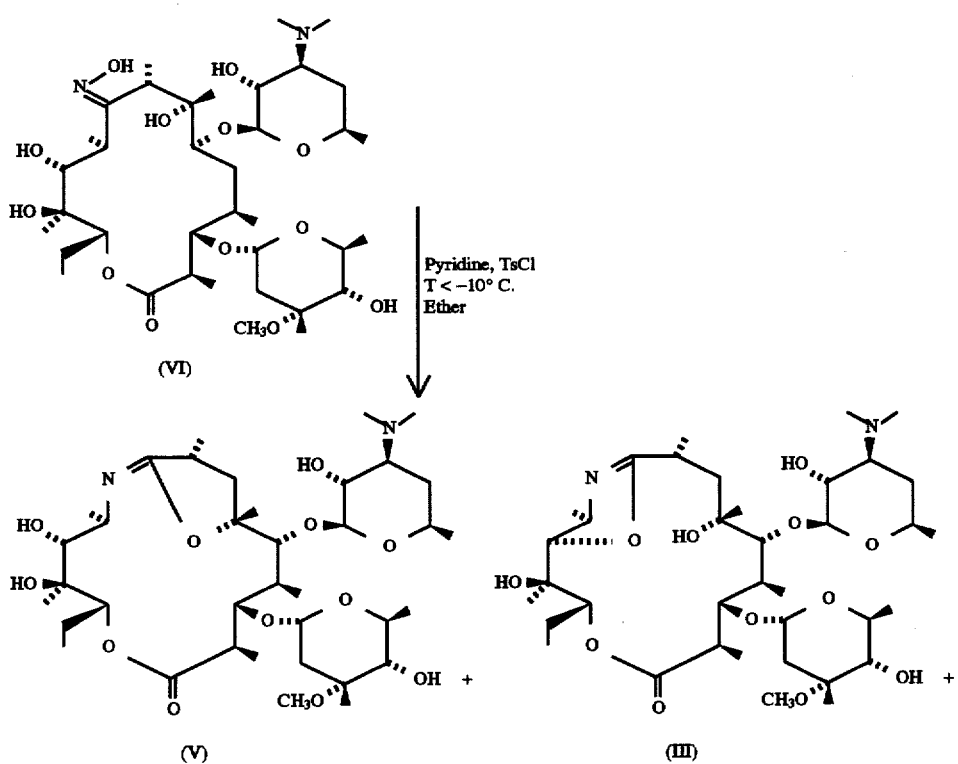

-continued
Scheme I
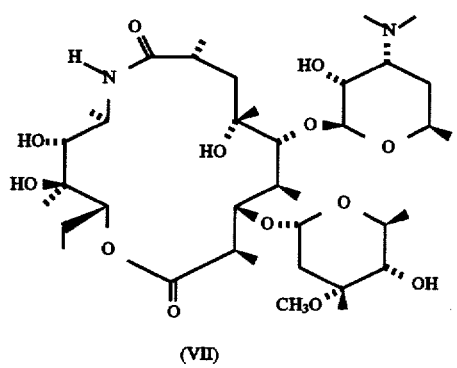
(VII)
STEP B
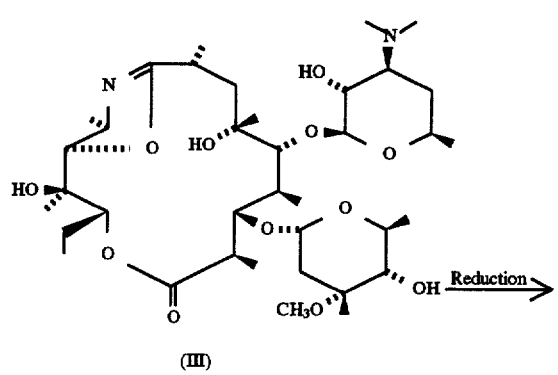
(III) —Reduction→
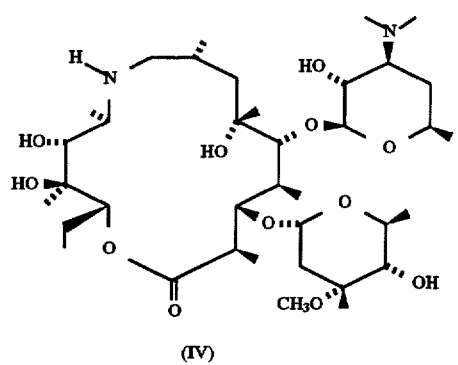
(IV)
STEP C
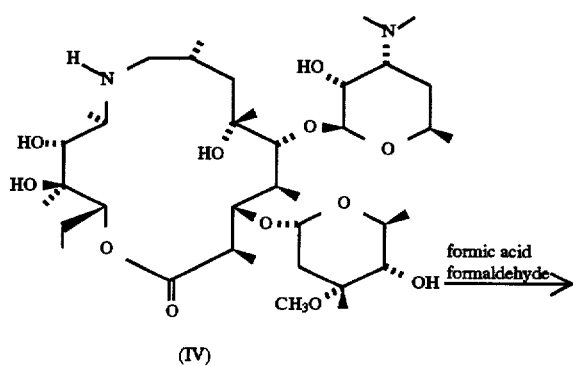
(IV) —formic acid / formaldehyde→

-continued
Scheme I

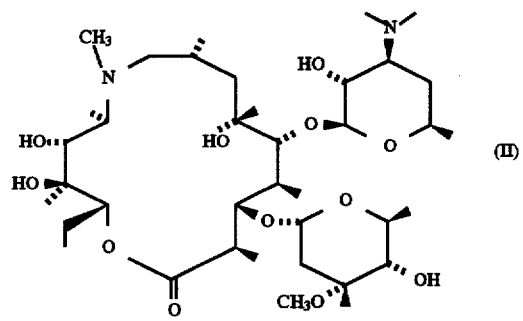

In the above scheme the starting material in step A, compound (VI) is the E-isomer of 9-deoxo-9-hydroxyimino erythromycin A and can be made by known procedures such as the straightforward reaction of Erythromycin A with hydroxylamine to produce the erythromycin E-oxime as the major isomer. The oxime is treated with tosyl chloride in the presence of pyridine as a base and in a suitable solvent such as a dialkyl ether (e.g. diethyl ether), thereby initially forming a corresponding O-tosyl oxime which is a suitable precursor in the Beckmann rearrangement of ketoximes. Importantly, the temperature should be maintained below −10° C. to favor formation of the 9,11 imino ether, compound III, over compound V, the 6,9 imino ether, and compound VII. Generally it is preferred to maintain the said temperature below −20° C., and most preferred to maintain the temperature below −40 ° C. At the low temperatures employed, and depending on the exact temperature employed, the reaction can take as long as several days to go to completion, although appreciable amounts of 9,11-imino ether III are available from workup of the reaction medium after much shorter reaction times, e.g., on the order of a day. The amount of tosyl chloride employed is at least equivalent to the amount of erythromycin A 9-E-oxime. To ensure completion of the reaction within a reasonable time the tosyl chloride can be used in excess, with a 2:1 equivalents ratio being preferred. The mixture will typically contain a mixture of compounds V, III, and VII, per Scheme I, Step A, which can be conventionally resolved by column chromatography separation, typically employing silica gel having a particle size of 230–400 mesh ASTM (commercially available, for example, as Silica Gel 60 from EM Science, Gibbstown, N.J.) with toluene, chloroform and triethylamine mixed in a ratio, respectively, of 20:1:1 as the eluting solvent system.

The fact that 9,11-imino ether III is made per Step A is surprising in view of literature precedent (Djokic et al., supra) wherein the erythromycin A 9-E-oxime of erythromycin A yielded 6,9-imino ether V only.

If appreciable amounts of 6,9-imino ether V are formed, it can be isomerized to compound III by dissolving it in a suitable solvent. Any of a number of solvents can be employed such as tetrahydrofuran, (THF), lower alcohols, (e.g. methanol, ethanol, or propanol) and halogenated hydrocarbons, with chlorinated hydrocarbons such as chloroform and methlene chloride being preferred. Deuterated analogs of the chlorinated solvents (e.g. deuterochloroform) can also be employed. To speed the rate of isomerization a catalytic amount of acid can be added to the reaction medium. The acid employed is not critical so long as it is not used in an amount which results in cleavage of either of the sugar fragments from the macrolide ring. Organic acids (e.g. trifluoroacetic acid, p-toluenesulfonic acid) or inorganic (hydrochloric, sulfuric) acids may be employed. It is preferred to use camphorsulphonic acid in an amount of 0.1 equivalent per equivalent of compound V at a temperature of from 15° C. to reflux, typically room temperature, for a period sufficient for isomerization to occur, typically a period of from about 12 hours to about 7 days or longer. Conversions of essentially 100% after about 7 days in deuterochloroform are feasible using this novel procedure. Total yields of the intermediate III of over 90%, based on the weight of the starting material, are facilely obtainable by combining compound III obtained directly from scheme I with compound III obtained by isomerizing compound V (also obtained from scheme I) in deuterochloroform.

Compound III can be reduced to compound IV, the direct precursor of azithromycin, by any of a number of conventional methods, but advantageously under much milder conditions than those known in the art for reducing macrolide imino ethers. Reduction can be effected under a hydrogen pressure of about 50 psi in the presence of platinum dioxide catalyst and in glacial acetic acid solvent. Yields approaching 90% are obtainable within reaction times of 48 hrs. Other methods of reduction employing conventional reducing agents such as sodium borohydride are also feasible. Reactions employing borohydride are typically conducted with stirring in a suitable solvent such as methanol at a temperature of 0° to room temperature, and employing at least one equivalent of borohydride. Workup can proceed as in Djokic et al., supra.

Compound IV can be methylated to obtain azithromycin as conventionally known in the art, for example by the Eschweiler-Clark reaction in which compound IV is reacted with a combination of formic acid and formaldehyde, most suitably performed with a 1–3 molar excess of formaldehyde and formic acid in an appropriate solvent, preferably in a halogenated hydrocarbon, e.g., chloroform or carbon tetrachloride. The reaction is generally conducted at reflux for a period of 2 to 8 hours. The azithromycin can be isolated by conventional means such as by simple solvent evaporation. If further purification is desired, such can be effected conventionally, for example column chromatography through silica gel employing an eluting solvent comprising, by volume, 3–10% chloroform, and 0.1–1% ammonium hydroxide.

The invention will now be illustrated by means of the following examples which are not, however, to be taken as limiting:

EXAMPLE 1

9-Deoxo-11-deoxy-9,11-epoxy-9,9a-dihydro-9a-aza-9a-homoerythromycin A (compound III)

METHOD A:

(Step A in Scheme I): Erythromycin A 9-oxime (6.11 g, 8.16 mmol) was dissolved in pyridine (45 ml) and cooled to −45° C. To this solution was added a precooled (−45° C.) solution of p-toluenesulfonyl chloride (3.2 g, 16.9 mmol) and pyridine (10 ml) in ether (25 ml). The reaction mixture was stirred at −45° C. for six hours and stood at −20° C. for 12 hours. The mixture was poured into cold water and stirred while the pH was adjusted to 5 with aqueous 2M HCl. The solution was extracted with 75 mL quantities of methylene chloride twice. After separation, the aqueous layer was extracted with 75 mL of chloroform at pH 7 and 9, respectively (pH adjusted with saturated aqueous solution of potassium carbonate). Each extract was separately washed with brine and dried over magnesium sulfate. The extract from pH 7, upon evaporation in vacuo, gave a slightly yellow solid, containing a mixture of 9-deoxo-11-deoxy-9,11-epoxy-9,9a-dihydro-9a-aza-9a-homoerythromycin A (compound III) and 9-deoxo-6-deoxy-6,9-epoxy-9,9a-dihydro-9a-aza-9a-homoerythromycin A (compound V) at 1.2/1 ration (4.69 g, 6.42 mmol, yield: 78.6%). The pH 9 extract was evaporated to yield a white solid containing 9a-aza-9a-homoerythromycin cyclic lactam (compounds VII) and 9-deoxo-6-deoxy-6,9-epoxy-9,9a-dihydro-9a-aza-9a-homoerythromycin A (V) at 2/1 ratio (0.49 g). A pure sample of III was obtained as follows: The mixture of V and III was dissolved in deuterochloroform and stirred at room temperature for 12 hours. After removal of solvent in vacuo, the residue was chromatographed on silica gel (eluent:toluene/CHCl$_3$/Et$_3$N 20:1:1) to afford the pure title compound as a white solid. $^{13}$CNMR(CDCl$_3$) 176.3, 102.2, 95.3, 83.0, 82.3, 81.1, 77.7, 76.7, 76.4, 75.1, 73.2, 72.7, 70.7, 69.4, 65.9, 65.1, 63.5, 49.3, 43.4, 40.3, 39.6, 34.6, 34.6, 29.8, 28.7, 25.0, 24.2, 21.7, 21.66, 21.0, 19.3, 18.1, 17.4, 11.3, 10.9. $^1$HNMR (CDCl$_3$, partial): 5.03 (br d, 1H), 4.81 (dd, J=10.1, 1.8 Hz, 1H), 4.61(d, J=7.3 Hz, 1h), 4.50 (D, J=4.7 Hz, 1H), 4.39 (d, J=8.5 Hz, 1H), 4.14 (m, 1H), 3.95 (m, 1H), 3.69 (d, J=5.9 Hz, 1H), 3.67 (s, 1H), 3.54 (m, 1H), 3.31 (s, 3H), 3.24 (m, 1H), 3.00 (t, J=9.7 Hz, 1H), 2.70 (m, 1H), 2.66 (m, 1H), 2.25 (s, 6H), 1.97 (s, 3H), 1.38 (d, J=6.6 Hz, 3H), 1.28 (s, 3H), 1.25 (d, J=6.4 Hz, 3H), 1.22 (s, 3H), 1.21 (S, 3H), 1.20 (s, 3H), 1.18 (s, 3H), 1.175 (s, 3H), 1.14 (d, J=7.2 Hz, 3H), 0.88 (t, J=7.2 Hz, 3H). FAB-mass:m/e:731, 573, 398, 158; high resolution mass calcd for C$_{37}$H$_{67}$N$_2$)$_{12}$: 731.4696; found 731.4744.

Method B:

A solution of 9-deoxo-6-deoxy-6,9-epoxy-9,9a-dihydro-9a-aza-9a-homoerythromycin A (compound V) (100 mg, 3.57 mmol) in CDCl$_3$ (1.5 ml) was stirred at room temperature for 36 hours. $^1$HNMR spectrum of an aliquot sample indicated that the reaction mixture contained 9-deoxo-6-deoxy-6,9-epoxy-9,9a-dihydro-9a-aza-9a-homoerythromycinA (compound V) and 9-deoxo-11-deoxy-9,11-deoxy-9,11-epoxy-9,9a-dihydro-9a-aza-9a-homoerythromycin A (compound III) at ratio 1.7/1. After seven days, the isomerization of compound V to III was complete, as indicated by $^1$HNMR spectrum. Evaporation of the solvent afforded the title compound in quantitative yield; it was identical with that obtained according to method A.

EXAMPLE 2

9-Deoxo-9a-aza-9a-homoerythromycin A (compound IV)

A solution of the title compound of example 1 (231 mg, 0.316 mmol) in acetic acid (20 ml) was hydrogenated over PtO$_2$ (13.1 mg, 0.058 mmol) under hydrogen (50 psi) at room temperature for 48 hours. The catalyst and the solvent were removed. The residue oil was dissolved in methylene chloride and washed with 10% aqueous potassium carbonate and brine, and dried over magnesium sulfate. The solvent evaporated in vacuo to afford the title compound pure (199 mg. 0.27 mmol, yield:85.8%); it was identical by comparison with a known sample of the title compound.

What is claimed is:

1. A compound having formula III

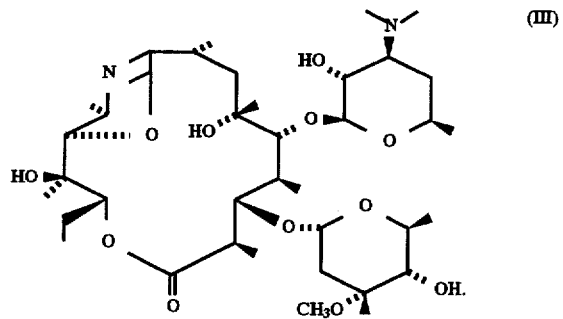

2. A process of making azithromycin, comprising reducing a compound of formula III to a compound of formula IV and thereafter N-methylating the said compound of formula IV at position 9a.

3. A process as defined in claim 2, wherein said compound of formula III is reduced with hydrogen in the presence of platinum dioxide catalyst.

4. A process as defined in claim 2, wherein said compound of formula IV is N-methylated by treating said compound of formula IV with a combination of formic acid and formaldehyde.

5. A method of making a compound having formula III

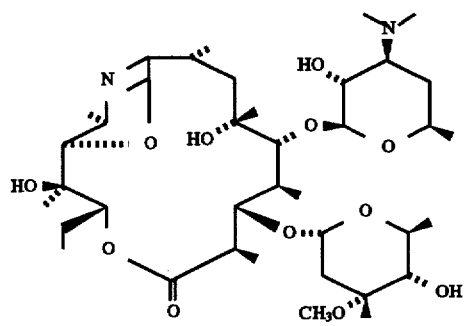

(III)

comprising treating a compound of formula VI comprising treating the E-isomer of formula VI

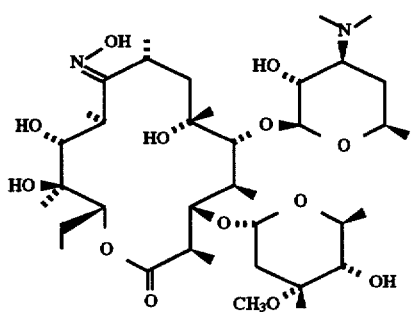

(VI)

with tosyl chloride in the presence of pyridine at a temperature less than about −10° C.

6. A process as defined in claim 5, wherein said temperature is less than about −20° C.

7. A process as defined in claim 6, wherein said temperature is less than about −40° C.

8. A process of making a compound having formula III

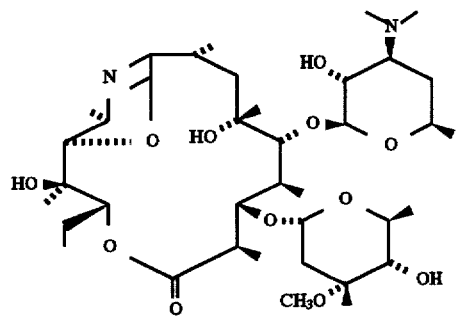

(III)

comprising dissolving a compound of formula V

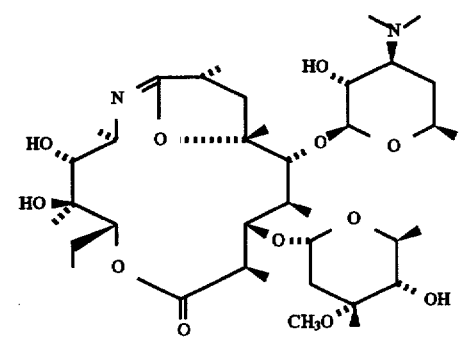

(V)

in a solvent for a time sufficient to produce said compound of formula III.

9. A process as defined in claim 8, wherein said isomerization is conducted for between about 12 hours and about 7 days.

10. A process as defined in claim 8, wherein said isomerization is conducted at a temperature between about 15° C. and the reflux temperature of deuterochloroform.

11. A process as defined in claim 10, wherein said isomerization is conducted at room temperature.

* * * * *